US010552577B2

(12) United States Patent
Schneider

(10) Patent No.: US 10,552,577 B2
(45) Date of Patent: Feb. 4, 2020

(54) MEDICATION REQUISITION FULFILLMENT SYSTEM AND METHOD

(71) Applicant: Baxter Corporation Englewood, Englewood, CO (US)

(72) Inventor: Dennis I. Schneider, Nashua, NH (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 481 days.

(21) Appl. No.: 14/424,959

(22) PCT Filed: Mar. 14, 2013

(86) PCT No.: PCT/US2013/031707
§ 371 (c)(1),
(2) Date: Feb. 27, 2015

(87) PCT Pub. No.: WO2014/035478
PCT Pub. Date: Mar. 6, 2014

(65) Prior Publication Data
US 2015/0235003 A1 Aug. 20, 2015

Related U.S. Application Data

(60) Provisional application No. 61/695,831, filed on Aug. 31, 2012.

(51) Int. Cl.
G06F 19/00 (2018.01)
(52) U.S. Cl.
CPC .............. G06F 19/3456 (2013.01)
(58) Field of Classification Search
CPC .. G06F 19/3456; G06F 19/00; G06F 19/3418; G06F 19/3462; G06F 19/328;
(Continued)

(56) References Cited

U.S. PATENT DOCUMENTS 641,748 A 1/1900 Smith
819,339 A 5/1906 Cleland
(Continued)

FOREIGN PATENT DOCUMENTS

JP 2003022322 1/2003
JP 2003022322 A 1/2003
(Continued)

OTHER PUBLICATIONS

Texas Administrative Code, Title 22, Part 15, Ch 291, Rules 20, 36, and 71-74. Feb. 10, 2004.
(Continued)

Primary Examiner — Hiep V Nguyen
(74) Attorney, Agent, or Firm — K&L Gates LLP

(57) ABSTRACT

A system and associated method are provided for fulfillment of medication requisitions corresponding to contained medication units. Requisition fulfillment logic may be included to provide decision data to a patient care provider for use in selecting one of a plurality of different fulfillment sites to fill a given medication requisition. A requisition router may route the medication requisition to a selected one of the plurality of fulfillment sites. The fulfillment sites may provide medication requisition metadata (e.g., data relating to the preparation and handling of medication units) to a medication requisition database in corresponding relation to the corresponding medication requisitions fulfilled by the fulfillment sites. The medication requisition metadata may be stored in the medication requisition database and accessed to facilitate enhanced management functionalities in relation to medication units dispensed by patient care providers.

35 Claims, 2 Drawing Sheets

(58) Field of Classification Search
CPC ............ G06F 17/30386; G06F 19/321; G06F 19/324; G06Q 50/22; G16H 20/10
USPC .......................................................... 705/2
See application file for complete search history.

(56) References Cited

U.S. PATENT DOCUMENTS

| | | |
|---|---|---|
| 3,426,150 A | 2/1969 | Tygart |
| 3,739,943 A | 6/1973 | Williamsen et al. |
| 3,742,938 A | 7/1973 | Stern |
| 3,756,752 A | 9/1973 | Stenner |
| 3,774,762 A | 11/1973 | Lichtenstein |
| 3,786,190 A | 1/1974 | Pori |
| 3,809,871 A | 5/1974 | Howard et al. |
| 3,810,102 A | 5/1974 | Parks, III et al. |
| 3,848,112 A | 11/1974 | Weichselbaum et al. |
| 3,858,574 A | 1/1975 | Page |
| 3,878,967 A | 4/1975 | Joslin et al. |
| 3,910,257 A | 10/1975 | Fletcher et al. |
| 3,910,260 A | 11/1975 | Sarnoff et al. |
| 3,921,196 A | 11/1975 | Patterson |
| 3,971,000 A | 7/1976 | Cromwell |
| 3,995,630 A | 12/1976 | Verrdonk |
| 3,998,103 A | 12/1976 | Bjorklund et al. |
| 4,032,908 A | 6/1977 | Rice et al. |
| 4,078,562 A | 3/1978 | Friedman |
| 4,144,496 A | 3/1979 | Cunningham et al. |
| 4,151,407 A | 4/1979 | McBride et al. |
| 4,156,867 A | 5/1979 | Bench et al. |
| 4,164,320 A | 8/1979 | Irazoqui et al. |
| 4,173,971 A | 11/1979 | Karz |
| 4,199,307 A | 4/1980 | Jassawalla |
| 4,270,532 A | 6/1981 | Franetzki et al. |
| 4,273,121 A | 6/1981 | Jassawalla |
| 4,282,872 A | 8/1981 | Franetzki et al. |
| 4,308,866 A | 1/1982 | Jelliffe et al. |
| 4,319,338 A | 3/1982 | Grudowski et al. |
| 4,320,757 A | 3/1982 | Whitney et al. |
| 4,354,252 A | 10/1982 | Lamb et al. |
| 4,369,780 A | 1/1983 | Sakai |
| 4,370,983 A | 2/1983 | Lichtenstein |
| 4,373,527 A | 2/1983 | Fischell |
| 4,381,776 A | 5/1983 | Latham, Jr. |
| 4,385,630 A | 5/1983 | Gilcher et al. |
| 4,398,289 A | 8/1983 | Schoate |
| 4,398,908 A | 8/1983 | Siposs |
| 4,414,566 A | 11/1983 | Peyton et al. |
| 4,416,654 A | 11/1983 | Schoendorfer et al. |
| 4,425,114 A | 1/1984 | Schoendorfer et al. |
| 4,428,381 A | 1/1984 | Hepp |
| 4,443,216 A | 4/1984 | Chappell |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,464,172 A | 8/1984 | Lichtenstein |
| 4,469,481 A | 9/1984 | Kobayashi |
| 4,475,901 A | 10/1984 | Kraegen et al. |
| 4,476,381 A | 10/1984 | Rubin |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,496,351 A | 1/1985 | Hillel et al. |
| 4,511,352 A | 4/1985 | Theeuwes et al. |
| 4,525,861 A | 6/1985 | Freeburg |
| 4,529,401 A | 7/1985 | Leslie et al. |
| 4,531,527 A | 7/1985 | Reinhold, Jr. et al. |
| 4,538,138 A | 8/1985 | Harvey et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,564,054 A | 1/1986 | Gustaysson |
| 4,590,473 A | 5/1986 | Burke et al. |
| 4,602,249 A | 7/1986 | Abbott |
| 4,619,653 A | 10/1986 | Fischell |
| 4,622,979 A | 11/1986 | Katchis et al. |
| 4,624,661 A | 11/1986 | Arimond |
| 4,636,950 A | 1/1987 | Caswell et al. |
| 4,637,817 A | 1/1987 | Archibald et al. |
| 4,650,469 A | 3/1987 | Berg et al. |
| 4,652,262 A | 3/1987 | Veracchi |
| 4,653,010 A | 3/1987 | Figler et al. |
| 4,676,776 A | 6/1987 | Howson |
| 4,681,563 A | 7/1987 | Deckert et al. |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,705,506 A | 11/1987 | Archibald |
| D293,135 S | 12/1987 | Medema et al. |
| 4,714,462 A | 12/1987 | DiComenico |
| 4,717,042 A | 1/1988 | McLaughlin |
| 4,718,576 A | 1/1988 | Tamura et al. |
| 4,722,224 A | 2/1988 | Scheller et al. |
| 4,722,349 A | 2/1988 | Baumberg |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |
| 4,741,732 A | 5/1988 | Crankshaw et al. |
| 4,741,736 A | 5/1988 | Brown |
| 4,756,706 A | 7/1988 | Kerns et al. |
| 4,759,756 A | 7/1988 | Forman |
| 4,778,449 A | 10/1988 | Weber et al. |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,545 A | 5/1989 | Epstein et al. |
| 4,829,524 A | 5/1989 | Yoshida |
| 4,830,018 A | 5/1989 | Treach |
| 4,831,562 A | 5/1989 | McIntosh et al. |
| 4,832,033 A | 5/1989 | Maher et al. |
| 4,835,372 A | 5/1989 | Gombrich et al. |
| 4,835,521 A | 5/1989 | Andrejasich et al. |
| 4,838,275 A | 6/1989 | Lee |
| 4,839,806 A | 6/1989 | Goldfischer et al. |
| 4,845,644 A | 7/1989 | Anthias et al. |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,898,209 A | 2/1990 | Zbed |
| 4,898,576 A | 2/1990 | Philip |
| 4,898,578 A | 2/1990 | Rubalcaba, Jr. |
| 4,901,728 A | 2/1990 | Hutchison |
| 4,908,017 A | 3/1990 | Howson et al. |
| 4,912,623 A | 3/1990 | Rantala et al. |

(56) References Cited

U.S. PATENT DOCUMENTS

| | | |
|---|---|---|
| 4,916,441 A | 4/1990 | Gombrich et al. |
| 4,922,922 A | 5/1990 | Pollock et al. |
| 4,925,444 A | 5/1990 | Orkin et al. |
| 4,933,843 A | 6/1990 | Scheller et al. |
| 4,937,777 A | 6/1990 | Flood et al. |
| 4,941,808 A | 7/1990 | Qureshi et al. |
| 4,943,279 A | 7/1990 | Samiotes et al. |
| 4,946,445 A | 8/1990 | Lynn |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,966,579 A | 10/1990 | Polaschegg |
| 4,967,928 A | 11/1990 | Carter |
| 4,968,295 A | 11/1990 | Neumann |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,993,506 A | 2/1991 | Angel |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,100,394 A | 3/1992 | Dudar et al. |
| 5,104,374 A | 4/1992 | Bishko et al. |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,169,642 A | 12/1992 | Brinker et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,762 A | 5/1993 | Charhut et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |
| 5,256,157 A | 10/1993 | Samiotes et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,325,478 A | 6/1994 | Shelton et al. |
| 5,327,341 A | 7/1994 | Whalen et al. |
| 5,331,549 A | 7/1994 | Crawford, Jr. |
| 5,336,245 A | 8/1994 | Adams et al. |
| 5,337,230 A | 8/1994 | Baumgartner et al. |
| 5,337,919 A | 8/1994 | Spaulding et al. |
| 5,338,157 A | 8/1994 | Blomquist |
| 5,339,421 A | 8/1994 | Housel, III |
| 5,339,821 A | 8/1994 | Fujimoto |
| 5,341,291 A | 8/1994 | Roizen et al. |
| 5,341,412 A | 8/1994 | Ramot et al. |
| 5,348,008 A | 9/1994 | Bornn et al. |
| 5,348,539 A | 9/1994 | Herskowitz |
| 5,349,675 A | 9/1994 | Fitzgerald et al. |
| 5,356,378 A | 10/1994 | Doan |
| 5,361,202 A | 11/1994 | Doue |
| 5,361,758 A | 11/1994 | Hall et al. |
| 5,366,896 A | 11/1994 | Margrey et al. |

(56) References Cited

U.S. PATENT DOCUMENTS

| | | |
|---|---|---|
| 5,366,904 A | 11/1994 | Qureshi et al. |
| 5,367,555 A | 11/1994 | Isoyama |
| 5,368,562 A | 11/1994 | Blomquist et al. |
| 5,370,612 A | 12/1994 | Maeda et al. |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Purvis et al. |
| 5,377,864 A | 1/1995 | Blechl et al. |
| 5,378,231 A | 1/1995 | Johnson et al. |
| 5,379,214 A | 1/1995 | Arbuckle et al. |
| 5,389,078 A | 2/1995 | Zalesky et al. |
| 5,390,238 A | 2/1995 | Kirk et al. |
| 5,392,951 A | 2/1995 | Gardner et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,404,292 A | 4/1995 | Hendrickson |
| 5,404,384 A | 4/1995 | Colburn et al. |
| 5,406,473 A | 4/1995 | Yoshikura et al. |
| 5,412,715 A | 5/1995 | Volpe |
| 5,415,167 A | 5/1995 | Wilk |
| 5,416,695 A | 5/1995 | Stutman et al. |
| 5,417,222 A | 5/1995 | Dempsey et al. |
| 5,420,977 A | 5/1995 | Sztipanovits et al. |
| 5,421,343 A | 6/1995 | Feng |
| 5,423,746 A | 6/1995 | Burkett et al. |
| 5,429,602 A | 7/1995 | Hauser |
| 5,431,201 A | 7/1995 | Torchia et al. |
| 5,431,299 A | 7/1995 | Brewer et al. |
| 5,431,627 A | 7/1995 | Pastrone et al. |
| 5,433,736 A | 7/1995 | Nilsson |
| 5,438,607 A | 8/1995 | Przygoda, Jr. et al. |
| 5,440,699 A | 8/1995 | Farrand et al. |
| 5,441,047 A | 8/1995 | David et al. |
| 5,445,294 A | 8/1995 | Gardner et al. |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,469,855 A | 11/1995 | Pompei et al. |
| 5,471,382 A | 11/1995 | Tallman et al. |
| 5,474,552 A | 12/1995 | Palti |
| 5,482,043 A | 1/1996 | Zulauf |
| 5,482,446 A | 1/1996 | Williamson |
| 5,485,408 A | 1/1996 | Blomquist |
| 5,490,610 A | 2/1996 | Pearson |
| 5,494,592 A | 2/1996 | Latham, Jr. et al. |
| 5,496,265 A | 3/1996 | Langley et al. |
| 5,496,273 A | 3/1996 | Pastrone et al. |
| 5,502,944 A | 4/1996 | Kraft et al. |
| 5,507,412 A | 4/1996 | Ebert et al. |
| 5,508,912 A | 4/1996 | Schneiderman |
| 5,509,318 A | 4/1996 | Gomes |
| 5,509,422 A | 4/1996 | Fukami |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,522,396 A | 6/1996 | Langer et al. |
| 5,522,798 A | 6/1996 | Johnson et al. |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,542,420 A | 8/1996 | Goldman et al. |
| 5,544,649 A | 8/1996 | David et al. |
| 5,544,651 A | 8/1996 | Wilk |
| 5,544,661 A | 8/1996 | Davis et al. |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | Mcilroy et al. |
| 5,588,815 A | 12/1996 | Zaleski, II |
| 5,589,932 A | 12/1996 | Garcia-Rubio et al. |
| 5,590,648 A | 1/1997 | Mitchell et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,609,575 A | 3/1997 | Larson et al. |
| 5,609,576 A | 3/1997 | Voss et al. |
| 5,613,115 A | 3/1997 | Gihl et al. |
| 5,619,428 A | 4/1997 | Lee et al. |
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,641,628 A | 6/1997 | Bianchi |
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |

(56) References Cited

U.S. PATENT DOCUMENTS

| | | |
|---|---|---|
| 5,661,978 A | 9/1997 | Holmes et al. |
| 5,664,270 A | 9/1997 | Bell et al. |
| 5,666,404 A | 9/1997 | Ciccotelli et al. |
| D385,646 S | 10/1997 | Chan |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,758,095 A | 5/1998 | Albaum et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,801,755 A | 9/1998 | Echerer |
| 5,803,906 A | 9/1998 | Pratt et al. |
| 5,805,442 A | 9/1998 | Crater et al. |
| 5,805,454 A | 9/1998 | Valerino et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,812,410 A | 9/1998 | Lion et al. |
| 5,814,015 A | 9/1998 | Gargano et al. |
| 5,815,566 A | 9/1998 | Ramot et al. |
| 5,818,528 A | 10/1998 | Roth et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,447 A | 11/1998 | Rieker et al. |
| 5,832,448 A | 11/1998 | Brown |
| 5,832,450 A | 11/1998 | Myers et al. |
| 5,833,599 A | 11/1998 | Schrier et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,884,273 A | 3/1999 | Sattizahn et al. |
| 5,884,457 A | 3/1999 | Ortiz et al. |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zimi et al. |
| 5,894,273 A | 4/1999 | Meador et al. |
| 5,895,371 A | 4/1999 | Levitas et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |
| 5,907,493 A | 5/1999 | Boyer et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,089 A | 6/1999 | Stevens et al. |
| 5,915,240 A | 6/1999 | Karpf |
| 5,919,154 A | 7/1999 | Toavs et al. |
| 5,921,938 A | 7/1999 | Aoyama et al. |
| 5,923,018 A | 7/1999 | Kameda et al. |
| 5,924,074 A | 7/1999 | Evans |
| 5,924,103 A | 7/1999 | Ahmed et al. |
| 5,927,540 A | 7/1999 | Godlewski |
| 5,931,791 A | 8/1999 | Saltzstein et al. |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |

(56) References Cited

U.S. PATENT DOCUMENTS

| | | |
|---|---|---|
| 5,941,829 A | 8/1999 | Saltzstein et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 6,068,156 A | 5/2000 | Liff et al. |
| 6,283,322 B1 | 9/2001 | Liff et al. |
| 6,330,491 B1 | 12/2001 | Lion |
| 6,438,451 B1 | 8/2002 | Lion |
| 6,471,089 B2 | 10/2002 | Liff et al. |
| 6,564,121 B1 | 5/2003 | Wallace et al. |
| 6,581,798 B2 | 6/2003 | Liff et al. |
| 6,711,460 B1 | 3/2004 | Reese |
| 6,735,497 B2 | 5/2004 | Wallace et al. |
| 6,776,304 B2 | 8/2004 | Liff et al. |
| 6,814,255 B2 | 11/2004 | Liff et al. |
| 7,006,893 B2 | 2/2006 | Hart et al. |
| 7,151,982 B2 | 12/2006 | Liff et al. |
| 7,427,002 B2 | 9/2008 | Liff et al. |
| 7,831,448 B1 | 11/2010 | Goodall et al. |
| 7,941,325 B2 | 5/2011 | Heald et al. |
| 7,991,507 B2 | 8/2011 | Liff et al. |
| 8,280,549 B2 | 10/2012 | Liff et al. |
| 8,374,887 B1 | 2/2013 | Alexander |
| 2002/0100762 A1 | 8/2002 | Liff et al. |
| 2003/0050731 A1 | 3/2003 | Rosenblum |
| 2004/0019794 A1 | 1/2004 | Moradi et al. |
| 2004/0172289 A1 | 9/2004 | Kozic et al. |
| 2004/0204954 A1 | 10/2004 | Lacko |
| 2005/0080651 A1 | 4/2005 | Morrison et al. |
| 2005/0177392 A1 | 8/2005 | Domashnev |
| 2006/0265245 A1 | 11/2006 | McCallie et al. |
| 2007/0088590 A1 | 4/2007 | Berkelhamer et al. |
| 2007/0088594 A1 | 4/2007 | Goodall et al. |
| 2007/0250341 A1 | 10/2007 | Howe et al. |
| 2008/0195416 A1* | 8/2008 | Tribble .............. G06Q 10/10 705/2 |
| 2010/0012546 A1 | 1/2010 | Togashi et al. |
| 2010/0057489 A1* | 3/2010 | Howe .............. G06F 19/328 705/2 |
| 2010/0094653 A1 | 4/2010 | Tribble et al. |
| 2010/0125461 A1 | 5/2010 | Heald et al. |
| 2011/0267465 A1 | 11/2011 | Alexander et al. |
| 2013/0173277 A1* | 7/2013 | Eller .............. G06Q 50/22 705/2 |

FOREIGN PATENT DOCUMENTS

| | | |
|---|---|---|
| JP | 2004078970 | 3/2004 |
| JP | 2004078970 A | 3/2004 |
| JP | 2004232557 A | 8/2004 |
| JP | 2005269257 A | 9/2005 |
| JP | 2010533927 | 10/2010 |
| WO | 2009012371 | 1/2009 |

OTHER PUBLICATIONS

Peterson, Charles D. and Anderson, Jr., Howard C.; "The North Dakota Telepharmacy Project: Restoring and Retaining Pharmacy Services in Rural Communities" Feb. 1, 2004.
Cato Reference Manual, Support for Trial Version (Abridged), Vienna, May 2004 Jun. 1, 2004.
Seifert et al.; "The Training of a Telepharmacist: Addressing the Needs of Rural West Texas," American Journal of Pharmaceutical Education 2004; 68 (3) Article 60. Jul. 16, 2004.
Cato Reference Manual, Vienna, May 2005 May 1, 2005.
Phillips, Jon, Associate Director of Telemedicine; "Telepharmacy at Texas Tech," presented Apr. 30, 2003, published at http://www.ttuhsc.edu/telemedicine/publication.htm at least by Jun. 22, 2003 Jun. 22, 2003.
International Search Report pertaining to International Application No. PCT/US2013/031707.
International Preliminary Report on Patentability to International Application No. PCT/US2013/031707.
English translation of KIPO's Notice of Final Rejection issued in related Korean Patent Application No. 10-2015-7007596.
Korean Office Action for Korean counterpart Application No. 10-2017-7036887; action dated Jan. 31, 2018; (12 pages).
Canadian Office Action for related Canadian Application No. 2,883,273; action dated Mar. 6, 2018; (8 pages).
Japanese Office Action for related Japanese Application No. 2017-106958; action dated Apr. 10, 2018; (3 pages).
Korean Office Action for related Korean Application No. 10-2017-7036887; action dated Jul. 31, 2018; (3 pages).
Korean Office Action and English translation for related Korean Application No. 10-2017-7036887; action dated Oct. 10, 2018; (7 pages).
Australian Examination Report for related Australian Application No. 2013309509; action dated Dec. 4, 2018; (6 pages).
Augstralian Office Action for related Australian Application No. 2013309509; action dated Feb. 19, 2019; (6 pages).
New Zealand Examination Report for related New Zealand Application No. 739406; report dated May 3, 2019; (4 pages).
KIPO's Second Notice of Final Rejection dated Nov. 21, 2017 in related Korean Patent Application No. 10-2015-7007596.
Canadian Office Action for related Canadian Application No. 2,883,273; action dated Jan. 21, 2019; (7 pages).
Korean Preliminary Rejection for related Korean Application No. 10-2018-7032745; action dated Dec. 17, 2018; (13 pages).

* cited by examiner

MEDICATION REQUISITION FULFILLMENT SYSTEM AND METHOD

RELATED APPLICATIONS

This application claims priority to U.S. Provisional Patent Application No. 61/695,831 filed Aug. 31, 2012, entitled "MEDICATION REQUISITION FULFILLMENT SYSTEM AND METHOD," which application is incorporated herein by reference in its entirety.

FIELD OF THE INVENTION

The present invention relates to a system and associated method for fulfillment of a medication requisition to be dispensed by a patient care provider for administration to a patient.

BACKGROUND OF THE INVENTION

Patient care providers routinely dispense medication units for administration to patients in the course of providing health care services. In this regard, the dispensing and administration of medication units may require authorization by a governing regulatory body. The medication units may be prepared and/or otherwise dispensed by a pharmacy located at or otherwise affiliated with a given patient care provider or by third-party source(s). For example, many hospitals have an onsite pharmacy from which medication units may be dispensed after preparation at the pharmacy.

A number of factors may present logistical challenges to a patient care provider in fulfilling medication requisitions. For example, each medication unit to be dispensed by a given patient care provider may have a different associated fulfillment timing requirement to ensure timely dispensing and administration of the medication unit to the corresponding patient. Additionally, the scope of inventory needed for a pharmacy to accommodate a wide range of potential medication units may be difficult to maintain, particularly in relation to medication unit components having a limited shelf-life, demanding handling/storage requirements and/or otherwise experiencing supply shortages. Also, the preparation of certain types of mediation units necessitates specialized equipment, facilities and skills that may not be commonly available, thereby limiting sourcing options. Further, cost efficiencies may be unavailable to many patient care providers.

In addition to the foregoing, an emphasis on detailed record-keeping for medication units continues to grow in the healthcare field. Such record-keeping may entail the obtainment and storage of various data pertaining to the preparation and handling of medication units. In this regard, the administrative burden associated with such record-keeping continues to increase.

Currently, existing approaches for obtaining medication units largely entail source selection processes in which limited and/or static data is utilized to make a selection and/or in which sourcing selection options are otherwise limited.

SUMMARY OF THE INVENTION

The present disclosure generally relates to an improved system and associated method for fulfillment of a medication requisition to be dispensed by a patient care provider for administration to a patient.

In one aspect, an improved system comprises a requisition generator and a requisition fulfillment logic provided for use by a patient care provider. The requisition generator may be employed to generate a medication requisition for at least one contained unit of a medication to be dispensed by the patient care provider and administered to a patient. The requisition fulfillment logic may be executed by a computer-based tool to process a medication requisition and provide decision data for use in selecting one of a plurality of different fulfillment sites to fulfill the medication requisition. The decision data may be based, at least in part, on one of medication requisition fulfillment cost data and/or medication requisition fulfillment timing data corresponding with each of the plurality of fulfillment sites. The system may further include a requisition router to route a given medication requisition to a selected fulfillment site that is selected from the plurality of fulfillment sites for preparation of the medication requisition.

Accordingly, the system relieves a user of the patient care provider from, and/or assists user of the patient care provider in, the mental task of e.g. keeping track of inventory/availability of medication units with relation to fulfillment sites. Even more, the user may obtain the medication unit that best suits the patient care provider's needs from the appropriate fulfillment site. Moreover, the system implements improved man machine interaction, since the requisition router may route the medication requisition to the selected fulfillment site without the necessity of an interaction with the user of the patient care provider. In the context of this application, the term user of a patient care provider may relate to a human person, such as and not limited to an employee or an owner of a patient care provider.

As may be appreciated, the provision of a system having requisition fulfillment logic to provide decision data may facilitate the realization of enhanced cost efficiencies and/or timely medication requisition fulfillment by a patient care provider. For example, the decision data may be provided to assist the patient care provider in assessing trade-offs between utilizing different fulfillment sites in relation to a given medication requisition.

In contemplated embodiments, at least one or more than one of the plurality of fulfillment sites may be located remotely relative to the patient care provider. Further, at least another one of the plurality of fulfillment sites may be located at a patient care provider site corresponding with the patient care provider. For example, the patient care provider may have a pharmacy onsite or otherwise affiliated therewith. Hence, the system may, in an automated manner, allow a user of the patient care provider to select the most appropriate of a number of fulfillment sites without the necessity of accessing the individual fulfillment site. Moreover, the user of the patient care provider can reduce processing power at the patient care provider's site, by accessing and/or using processing power of one or more fulfillment sites.

In contemplated implementations, the patient care provider may comprise an entity that is authorized by a governing regulatory body to dispense medication requisitions. Further, the patient care provider may be an entity that is authorized by a governing regulatory body to prepare medication requisitions.

By way of primary example, the patient care provider may comprise one of the following:
 an acute care site;
 a hospital;
 a home infusion pharmacy;
 a physician office; or, a free-standing infusion clinic.

In relation to the contemplated system, a contained medication unit corresponding with a given medication requisition may be obtained by a patient care provider from a selected fulfillment site for dispensing by the patient care provider for administration to a patient. In this regard, the contained medication unit may comprise one of the following:

- a patient specific unit comprising a medication unit designated for administration to a specific patient;
- a non-patient specific unit comprising a medication unit to be subsequently designated for administration to a specific patient; or,
- a medication component source unit to be used in the preparation of a patient specific unit or a non-patient specific unit (e.g., that will be designated for administration to a specific patient after preparation).

In some instances, the contained medication unit may comprise a nutritional supplement or a component of a nutritional supplement that requires administration by the patient care provider. By way of example, a contained medication unit may comprise a parenteral nutrition supplement (e.g., a total parenteral nutrition or total nutrient admixture).

In some implementations, a contained medication unit may be received by the patient care provider from a remote fulfillment site, wherein the contained medication unit may be associated with a kit comprising a plurality of contained medication units (e.g., a container used for handling the corresponding plurality of medication units). The association may be obtained or defined in a database and/or a table of a database that identifies for each contained medication unit a corresponding kit. Accordingly, for each contained medication unit and for each kit there may be a direct relation between exactly one specific contained medication unit and one specific kit. In this regard, the different medication requisitions corresponding with the plurality of contained medication units comprising the kit may be associated with a corresponding kit identifier, thereby facilitating various record-keeping functionalities, e.g., the obtainment and maintenance of certain medication requisition metadata referenced hereinbelow. For example, a kit identifier (e.g., a machine-readable marking on a container used for handling the corresponding plurality of medication units) may be utilized to facilitate data collection in relation to the location, handling, etc., of the associated medication units. Accordingly, the system allows in a simple and efficient manner to provide a specific contained medication unit with a number (i.e., a kit of) contained medication units, and maintain records relating thereto, without needing to separately obtain/record information for each individual/specific medication unit (e.g., in relation to location, handling, etc.). In particular, in view of the complexity of organizing a chain of products, the system provides in a simple and automated manner obtaining a specific medication unit while providing a kit of medication units. The system may particularly comprise a computing environment implementing or being part of the requisition generator and/or the requisition fulfillment logic and/or the requisition router.

As noted, the system may comprise requisition fulfillment logic to provide decision data based in part on at least one of medication requisition fulfillment cost data and/or medication requisition fulfillment timing data corresponding with each of a plurality of fulfillment sites. Such data may be stored and otherwise maintained in a medication requisition database.

The medication requisition fulfillment timing data may comprise at least one of the following:

- medication requisition fulfillment lead time data;
- medication requisition availability data;
- medication requisition delivery schedule data;
- medication requisition efficacy timing data; and/or,
- medication unit component efficacy timing data.

The medication requisition fulfillment cost data may comprise data indicative of a cost for fulfillment of a given medication requisition by a given fulfillment site.

In contemplated system embodiments, each of the plurality of fulfillment sites may provide all or at least a portion of the medication requisition fulfillment cost data and/or medication requisition fulfillment timing data corresponding with the given fulfillment site. More particularly, such data (simply referred to as medication requisition data) may be provided by the fulfillment sites to the medication requisition database. For example, the data may be provided on a periodic, request/response, or other basis. By way of further example, the data may be provided in relation to predetermined types or otherwise specified medication units.

In some embodiments the requisition fulfillment logic may comprise one or more algorithms (e.g., stored in a computer-readable medium) for processing the medication requisition (e.g., by a computer) in relation to medication requisition fulfillment cost data and/or medication requisition fulfillment timing data stored at the medication requisition database. In one approach, an algorithm may provide for the selective establishment of weighting parameters associated with each of medication requisition fulfillment cost data and/or medication requisition fulfillment timing data (e.g., via software program instructions/user input).

In some applications, the requisition fulfillment logic may be provided to be customizable by a given patient care provider. By way of example, a given patient care provider may set algorithm weighting parameters and/or may define additional logic parameters.

In certain implementations, the requisition fulfillment logic may be operable to automatically select a fulfillment site to fulfill a given medication requisition based on the generated decision data. As may be appreciated, such automated selection functionality may be established in relation to predetermined types of medication requisitions. Further, in some embodiments, the requisition router may be operable to automatically route medication requisitions to an automatically selected fulfillment site. Accordingly, without the need of human interaction, the system may allow for efficient drug medication requisition fulfillment. In particular, the efficiency may be improved by the system becoming more failsafe as the router is not prone to errors a human may make.

In some arrangements, the selected fulfillment site may be adapted to selectively, automatically and/or semi-automatically reject a given medication requisition routed to it (e.g., in the event of unforeseen or other circumstances). In turn, a requisition rejection may be communicated by the fulfillment site (e.g., in a selective, automatic and/or semi-automatic manner) to the fulfillment logic and medication requisition database, wherein the requisition fulfillment logic is further utilized to provide decision data for use selecting a different fulfillment site. Correspondingly, the medication requisition database may be updated in relation to the medication requisition.

In contemplated embodiments, the fulfillment site selected to fulfill a given medication requisition may be adapted to provide medication requisition metadata to a medication requisition database in relation to fulfillment of the medication requisition. In this regard, the selected fulfillment site may follow predetermined procedures and/or utilize data collection tools to obtain and provide medication requisition metadata in relation to the preparation, handling, etc., of a medication unit corresponding with a given medication requisition, and to provide medication requisition metadata to the medication requisition database. In turn, the system may be provided so that the patient care provider corresponding with a given medication requisition may access at least a portion of the corresponding medication requisition metadata from the medication requisition database.

The medication requisition metadata may comprise one or more of the following types of data:
- medication source data indicative of at least one of:
  - a manufacturer of a component of the contained medication unit corresponding to the medication requisition,
  - a lot number of a component of the contained medication unit corresponding to the medication requisition,
  - an expiration date of a component of the contained medication unit corresponding to the medication requisition,
  - a serial number of a component of the contained medication unit corresponding to the medication requisition, or
  - a drug code indicative of the identity of a component of the contained medication unit corresponding to the medication requisition;
- chain of custody data indicative of at least one of:
  - a listing of entities in possession of a component of the contained medication unit corresponding to the medication requisition or the contained medication unit corresponding to the medication requisition,
  - a listing of users that have taken an action with respect to the contained medication unit corresponding to the medication requisition, wherein the listing of users is correlated to specific actions taken by each user, or
  - tracking information corresponding to physical movement of a component of the contained medication unit corresponding to the medication requisition or the contained medication unit corresponding to the medication requisition;
- fulfillment data indicative of at least one of:
  - image data corresponding with a component of the contained medication unit corresponding to the medication requisition or the contained medication unit corresponding to the medication requisition,
  - scanned data obtained from a component of the contained medication unit corresponding to the medication requisition,
  - analytic data regarding a component of the contained medication unit corresponding to the medication requisition or the contained medication unit corresponding to the medication requisition,
  - pharmacist review data corresponding with at least one pharmacist review of a component of the contained medication unit corresponding to the medication requisition or the contained medication unit corresponding to the medication requisition,
  - compliance data corresponding with best practices associated with a component of the contained medication unit corresponding to the medication requisition or the contained medication unit corresponding to the medication requisition,
  - sterility assessment data corresponding to a component of the contained medication unit corresponding to the medication requisition or the contained medication unit corresponding to the medication requisition,
  - a listing of actions corresponding to a component of the contained medication unit corresponding to the medication requisition or the contained medication unit corresponding to the medication requisition,
  - time stamp data corresponding to actions corresponding to a component of the contained medication unit corresponding to the medication requisition or the contained medication unit corresponding to the medication requisition, or
  - a listing of life cycle events taken with respect a component of the contained medication unit corresponding to the medication requisition or the contained medication unit corresponding to the medication requisition; or
- environmental data indicative of at least one of:
  - a temperature to which a component of the contained medication unit corresponding to the medication requisition or the contained medication unit corresponding to the medication requisition has been exposed,
  - a temperature to which and corresponding time period for which a component of the contained medication unit corresponding to the medication requisition or the contained medication unit corresponding to the medication requisition has been exposed,
  - whether a component of the contained medication unit corresponding to the medication requisition or the contained medication unit corresponding to the medication requisition is refrigerated,
  - whether a component of the contained medication unit corresponding to the medication requisition or the contained medication unit corresponding to the medication requisition is frozen,
  - a temperature profile experienced by a component of the contained medication unit corresponding to the medication requisition or the contained medication unit corresponding to the medication requisition, or
  - accelerometer data corresponding to forces experienced by a component of the contained medication unit corresponding to the medication requisition or the contained medication unit corresponding to the medication requisition.

As may be appreciated, the obtainment and accessibility of medication requisition metadata may enhance the management functionality of the medication unit fulfillment system. The medication requisition metadata, in particular used and/or stored by a computer, relieves the user of the patient care provider from, and/or assists the user of the patient care provider in, the (mental) task of keeping track of and/or organizing the above mentioned data. In particular, without the (computer aided) system according to this application, the above mentioned data management and data processing would not be possible.

In various implementations, the contemplated system may include a distributed medication requisition management system that includes a distributed medication requisition management client at each of the plurality of fulfillment sites and in operative communication with the requisition router so as to receive medication requisitions from the requisition router. In turn, the system may further include a medication requisition management network that includes the distributed medication requisition management clients, the medication requisition database, and the requisition router. In such implementations, the system may be maintained so that at least portions of the corresponding medication requisition metadata are located at separate physical locations.

In another aspect, a distributed medication requisition management system may comprise a requisition generator to generate a medication requisition for at least one contained unit of a medication for dispensing by a patient care provider, and a medication requisition database operable to store the medication requisition. The system may further include a plurality of medication requisition management clients resident in a plurality of fulfillment sites capable of fulfilling a medication requisition. A medication requisition management network may be provided in operative communication with each of the plurality of medication requisition management clients, the medication requisition database, and the requisition generator, wherein the medication requisition management network is operable to provide the medication requisition to the medication requisition management client of a selected fulfillment site of the plurality of fulfillment sites. The system may be provided so that the patient care provider obtains a contained medication unit corresponding with the medication requisition from the selected fulfillment site for dispensing and administration to a corresponding patient, and wherein the selected fulfillment site provides medication requisition metadata to the medication requisition management network for storage in the medication requisition database in corresponding relation to the medication requisition.

As may be appreciated, various ones and combinations of the functionalities noted hereinabove may be utilized in the distributed medication requisition management system.

In a further aspect, a method for fulfillment of a medication requisition to be dispensed by a patient care provider, for administration to a patient is provided. In some embodiments, the method may include generating a medication requisition by use of a requisition generator by a patient care provider, wherein the medication requisition is for at least one contained unit of a medication for administration to a patient. The method may further comprise processing the medication requisition, by use of requisition fulfillment logic by a patient care provider and executed by a computer-based tool, wherein the processing provides decision data for use in selecting one of a plurality of fulfillment sites to fulfill the medication requisition. In this regard, decision data may be based at least in part on one of medication requisition fulfillment cost data or medication requisition fulfillment timing data corresponding to each of the plurality of fulfillment sites. Further, the method may include routing of the medication requisition by a requisition router to a selected fulfillment site selected from the plurality of fulfillment sites for preparation of the medication requisition.

In some embodiments, the method may further include selecting automatically, by operation of the requisition fulfillment logic, the selected fulfillment site at least partially based on the decision data. Additionally, or alternatively, the method may further comprise routing automatically, by operation of the router, the medication requisition to the selected fulfillment site for fulfillment of the medication requisition. In various method embodiments, the method may employ a system comprising any of the system features described herein.

According to yet another aspect, a computer program product is provided that can be stored on a computer readable medium and/or can be implemented as computer processable data stream, wherein the computer program product comprises computer processable instructions, which instructions when read in the memory of a computer and executed by the computer cause the computer to carry out the method(s) as described in general above, and in more specific examples below.

Numerous additional features and advantages of the present invention will become apparent to those skilled in the art upon consideration of the embodiment descriptions provided hereinbelow.

DETAILED DESCRIPTION

Figure 1:
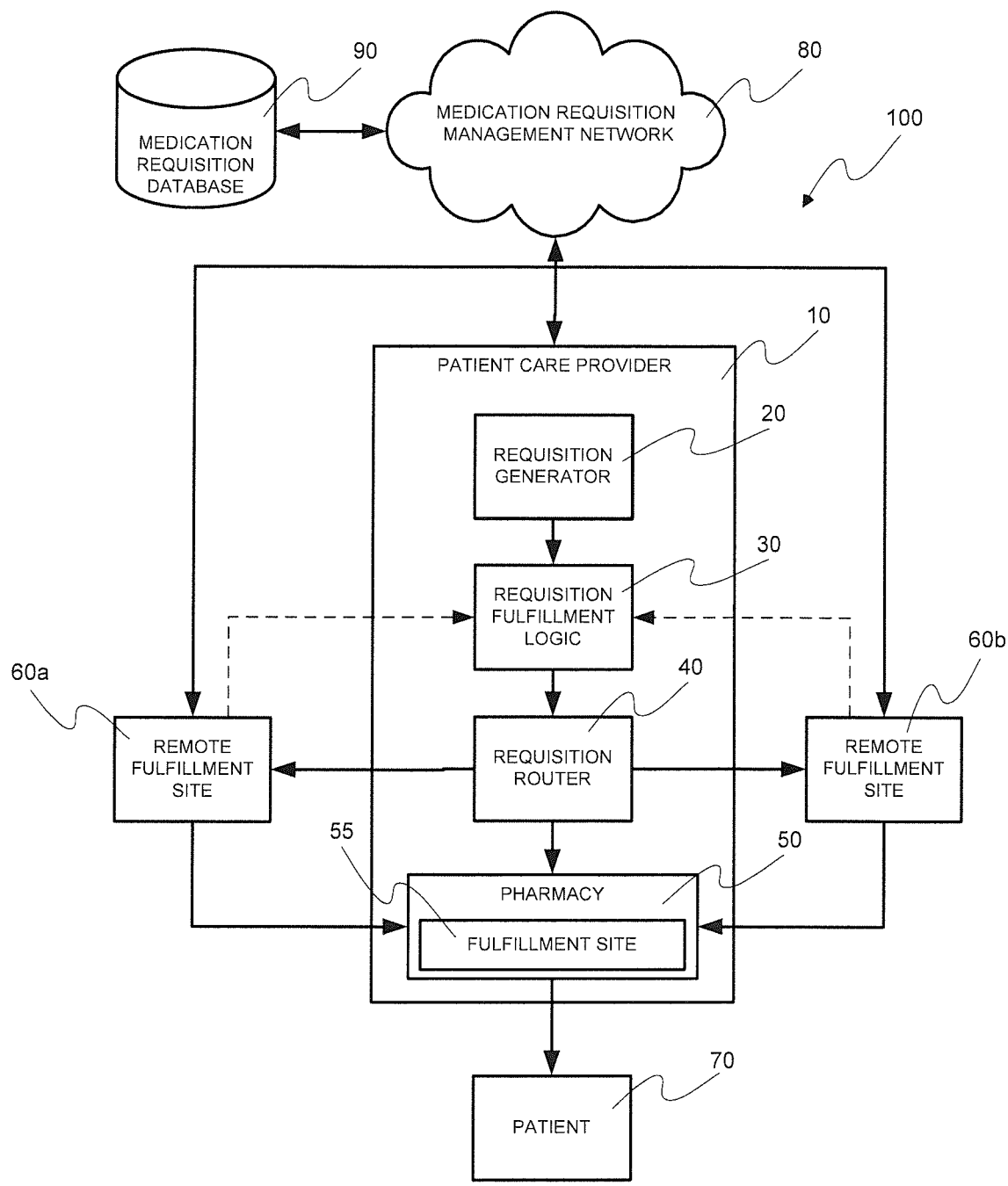
FIG. 1 illustrates an embodiment of a system for fulfillment of medication requisitions.

FIG. 1 illustrates an embodiment of a system 100 for fulfillment of a medication requisition. The medication requisition may correspond to at least one contained unit of a medication. The contained unit may comprise, for instance, one of the following:
 a syringe;
 a vial;
 a bag; or,
 another medication container used in the administration of a medication to a patient or used in the course of preparation of a medication for administration to a patient.

The system 100 may include a number of components that may be used to generate a medication requisition, to prepare decision data for use in the selection of a fulfillment site for fulfillment of the medication requisition, and to route a given medication requisition to a selected fulfillment site. In this regard, the components of the system 100 may include a requisition generator 20, requisition fulfillment logic 30, and a requisition router 40, respectively. By way of example, the requisition generator 20, requisition fulfillment logic 30, and a requisition router 40 may be located at a patient care provider 10.

The requisition generator 20 may generate a medication requisition corresponding to a medication unit that is to be used or dispensed by the patient care provider 10 for administration to a patient 70. The requisition generator 20 may be operable to generate the medication requisition in an automated or partially automated manner based on an order comprising a data stream. By way of example, the order may correspond with a medication prescribed by a physician.

In one approach, the requisition generator 20 may be operable to parse or otherwise derive data from a data stream to generate the medication requisition. Additionally or alternatively, the requisition generator 20 may generate a medication requisition based on data that is received directly from a user (e.g., by way of data entry via a user interface).

The requisition generator 20 may be operable to provide the medication requisition for processing by requisition fulfillment logic 30. Requisition fulfillment logic 30 may comprise a computer-based tool (e.g., including hardware and/or software) for providing decision data for use in selecting one of a plurality of fulfillment sites to fulfill a given medication requisition. The computer-based tool may comprise a memory operable to store non-transitory machine-readable instructions that may be executed by a processor. Requisition fulfillment logic 30 may further include or access a database that may be used by the requisition fulfillment logic 30 to produce the decision data.

The data utilized by requisition fulfillment logic 30 to provide the decision data may at least include medication requisition preparation cost data and/or medication requisition preparation timing data that corresponds to a plurality of potential fulfillment sites that have the ability to fulfill the medication requisition. For example, as shown in FIG. 1, remote fulfillment site 60a, remote fulfillment site 60b, or fulfillment site 55 may all be potential fulfillment sites for fulfillment of medication requisitions.

In this regard, the requisition fulfillment logic 30 may provide the decision data to a user (e.g., provided to a user at the patient care provider 10 via a user interface device). The user may then select one of the plurality of fulfillment sites for fulfillment of the medication requisition (e.g., via input at a user interface). In an embodiment, requisition fulfillment logic 30 may automatically select a fulfillment site at least partially based on the decision data for a given medication requisition. Optionally, a determination as to whether a fulfillment site is selected by a user or automatically selected may at least partially depend upon an identifiable characteristic of a given medication requisition (e.g., dependent upon medication type, medication amount, timing requirements, or other data associated with the medication requisition). In this regard, potential time and cost savings may be realized.

As noted, a requisition router 40 may be provided to route the medication requisition to the selected fulfillment site for fulfillment of the medication requisition. As schematically presented in FIG. 1, at least one onsite fulfillment site (e.g., fulfillment site 55) and/or at least one offsite fulfillment site (e.g., fulfillment sites 60a, 60b) may be available for selection to fulfill a given medication requisition.

Regardless of the relative location of the selected fulfillment site, the requisition router 40 may be operable to communicate the medication requisition to the selected fulfillment site. The requisition router 40 may receive the identity of the selected fulfillment site from a user (e.g., a user at the patient care provider 10) or may automatically route the medication requisition order to the selected fulfillment site based on the automatic selection of a fulfillment site by the requisition fulfillment logic 30.

One or more of the fulfillment sites 60a and 60b may be adapted to selectively, automatically and/or semi-automatically reject a given medication requisition routed to it (e.g., in the event of unforeseen circumstances). In turn, a requisition rejection may be communicated by the fulfillment site 60a or 60b (e.g., in a selective, automatic and/or semi-automatic manner) to requisition fulfillment logic 30 and medication requisition database 90, wherein the requisition fulfillment logic 30 is further utilized to provide decision data for use selecting a different fulfillment site. Correspondingly, the medication requisition database 90 may be updated in relation to the medication requisition.

As stated above, the fulfillment sites may include one or more remote fulfillment sites 60a and 60b located remotely relative to the patient care provider 10. Furthermore, the patient care provider 10 may include a patient care provider site that may include a pharmacy 50. In turn, the pharmacy 50 may include a fulfillment site 55 located in the pharmacy 50. It may also be appreciated that the patient care provider 10 may be affiliated with a pharmacy 50 that is located offsite relative to the patient care provider site. In any regard, each of the fulfillment sites 55, 60a, and 60b may be capable of fulfilling a medication requisition and providing the medication unit corresponding to the medication requisition to the pharmacy 50. In turn, the pharmacy 50 may be operable to dispense the medication unit for administration to the patient 70.

Additionally, as depicted in FIG. 1, a medication requisition management network 80 may be in operative communication with remote fulfillment sites 60a and 60b, as well as the patient care provider 10. The medication requisition management network 80 may also be in operative communication with a medication requisition database 90. The medication requisition database 90 may be operable to store one or more sets, or portions, of data in corresponding relation to each given medication requisition.

The medication requisition database 90 may be located in a single location that is either remote from or local to one or more of the patient care provider site or remote fulfillment sites. The medication requisition database 90 may also be provided at a separate location distinct from either the patient care provider site or remote fulfillment site. Further, the medication requisition database 90 may comprise a number of portions or instances that may each be located at separate locations corresponding to or separate from the patient care provider site or remote fulfillment sites.

For example, the medication requisition database 90 may store medication requisition metadata related to the medication requisition. Furthermore, the medication requisition database 90 may store the medication requisition fulfillment cost data and the medication requisition fulfillment timing data employed by the requisition fulfillment logic 30 to produce the decision data for use in selecting one of the plurality of fulfillment sites to fulfill the medication requisition. In this regard, the remote fulfillment sites 60a and 60b may be in operative communication with the medication requisition database 90 to provide medication requisition fulfillment cost data and medication requisition fulfillment timing data corresponding to each respective fulfillment site to the medication requisition database 90.

The medication requisition database 90 may be located remotely from the remote fulfillment sites 60a and 60b as well as the patient care provider 10. Alternatively, the medication requisition database 90 may be located at one of the remote fulfillment sites 60a or 60b or at the patient care provider 10. In any regard, access to the medication requisition database 90 may be facilitated via the medication requisition management network 80.

As may be appreciated, the patient care provider 10 may include an entity authorized by a governing regulatory body (e.g., a pharmacy board) to dispense and prepare medication units for administration to patients. In this regard, the patient care provider may include an authorized entity capable of compounding or otherwise preparing contained medication units for administration to patients. Primarily, examples of patient care providers include the following:

an acute care site;
a hospital;
a home infusion pharmacy;
a physician office;
a free standing infusion clinic; or,
or other appropriate healthcare entity authorized to prepare medications.

In an application, the patient care provider may be a hospital having an affiliated pharmacy. It may be appreciated that the affiliated pharmacy may be located onsite with respect to the hospital or the hospital may be affiliated with an offsite pharmacy. In either regard, the medication unit associated with the medication requisition may be administered to the patient at the patient care provider site by the patient care provider. In the case of an offsite pharmacy, the offsite pharmacy may service a plurality of different affiliated hospital sites.

As stated above the medication requisitions generated by the requisition generator 20 may each correspond to a contained unit of a medication for administration to patient. The contained medication unit may be a patient specific unit comprising a medication unit designated for administration to a specific patient. In an embodiment, the contained medication unit may include a non-patient specific unit to be subsequently designated for administration to a specific patient. In an embodiment, a contained medication unit may be a medical source unit (e.g., a compounded or other ingredient) to be used in the preparation of a patient specific unit and/or a non-patient specific unit.

In various embodiments, the contained medication unit may correspond to a variety of different substances that require licensure or other authorization by governing body to prepare. Examples of contained medication units that may correspond to medication requisitions include:

compounded sterile products;
injectable medications;
chemotherapy preparations; or,
nutritional supplements requiring administration by a patient care provider (e.g., sterile injectable nutritional supplements).

Nutritional supplements may include total parenteral nutrition (TPN) or components of TPN. Furthermore, nutritional supplements may include partial nutritional supplements. The nutritional supplements may include a pre-mix bag, base and additive components separately or in combination, or other forms of nutritional supplements or components thereof. The nutritional supplements may be for administration via intravenous injections, in an edible form, or for use with a feeding tube or the like.

The medication requisition generated by the requisition generator 20 may include data indicative of one or more properties or requirements of the medication requisition. In this regard, the medication requisition may include:

a medication identity;
a medication amount;
a medication concentration;
information associated with a patient to whom the medication unit associated with the medication requisition is to be administered;
scheduling information (e.g., an administration time) for the medication unit associated with medication requisition; or
other appropriate information regarding the medication unit associated with the medication requisition.

In one embodiment, the medication requisition including or associated with any of the foregoing data or other relevant data corresponding to the medication requisition may be stored in the medication requisition database 90.

In any regard, the requisition fulfillment logic 30 may receive the medication requisition and be operable to compare the medication requisition (e.g., medication identity, medication amount, medication concentration, scheduled dispensation time, etc.) in relation to the medication requisition preparation timing data and/or the medication requisition preparation cost data for the plurality of fulfillment sites to determine the decision data for use in determining which fulfillment site may be capable of, or best suited to, fulfill the medication requisition.

In one example, the requisition fulfillment logic 30 may determine which fulfillment site or sites from the plurality of fulfillment sites is capable of fulfilling a medication requisition based on whether a fulfillment site can fulfill the medication requisition prior to the scheduled dispensation time for the medication requisition. In this regard, the medication requisition fulfillment timing data may include, for example:

medication requisition fulfillment lead time data;
medication requisition availability data;
medication requisition delivery schedule data;
medication requisition efficacy timing data; or
medication unit component efficacy timing data.

Of those fulfillment sites capable of fulfilling a medication requisition in accord with the scheduled administration time, the medication requisition fulfillment cost data may in turn be used to determine which of the eligible fulfillment sites represent the lowest cost for the fulfillment of the medication requisition. In this regard, the fulfillment site with the lowest cost of fulfillment capable of fulfilling in time for the scheduled administration of the medication unit associated with the medication requisition may be identified as the selected fulfillment site. However, other logic may be applied that may for example, strike different balances between considerations of medication requisition fulfillment cost data, medication requisition fulfillment timing data, or other relevant information for use in producing the decision data. In this regard, the applied logic may be as selectively established by a given patient care provider 10. For example, an algorithm may be established with weighting parameters associated with the relative importance of the medication requisition fulfillment cost data relative to the medication requisition fulfillment timing data. In an example, the patient care provider 10 may predetermine or have control over the weighting of the data. Other factors or data may also be weighted in the algorithm used to arrive at the decision data.

In contemplated implementations, the patient care provider 10 may be able to customize the algorithm and/or factors considered in providing a decision data. For example, the patient care provider may provide overriding conditions that dictate selection of a selected fulfillment site regardless of the decision data. The overriding condition may be based on medication requisitions generated in a specific period, of a specific kind, for administration in a certain period, or other factors related to the medication requisition or fulfillment of the medication requisition.

With further respect to the requisition router 40, as discussed above, the requisition router 40 may be operable to route a medication requisition to a selected one of a plurality of fulfillment sites. As such, the requisition router 40 may be in direct communication with each of the remote fulfillment sites 60*a* and 60*b* as well as the fulfillment site 55 located in the pharmacy 50 of the patient care provider 10.

In an embodiment, the routing of medication requisitions from the requisition router 40 to the selected fulfillment site may occur in substantially real-time upon selection of the fulfillment site. In an embodiment, the routing of a medication requisition to the selected fulfillment site may occur periodically as either initiated by the requisition router 40 or the selected fulfillment site. The requisition router 40 may be operable to transmit a group or batch of individual medication requisitions to a single fulfillment site simultaneously in the case where the fulfillment site has been selected as the selected fulfillment site for a number of medication requisitions.

In an embodiment, the requisition router 40 may provide medication requisitions to a fulfillment site by way of the medication requisition management network 80. In this regard, rather than direct communication between the requisition router 40 and remote fulfillment sites 60*a* and 60*b*, the requisition router 40 may communicate with remote fulfillment sites 60*a* and 60*b* by way of the medication requisition management network 80.

Each fulfillment site may be operable to provide medication requisition metadata to the medication requisition database 90 (e.g., either directly or via the medication requisition management network 80) regarding medication requisition fulfillment at the fulfillment site. The medication requisition metadata may include details regarding the composition, preparation, transportation, or other data concerning the medication requisition. The medication requisition metadata may be maintained in corresponding relation to a medication requisition record in the medication requisition database 90. The medication requisition metadata may be periodically updated by a fulfillment site before, during, or after fulfillment of the medication requisition. This may be particularly advantageous in the case of remote fulfillment sites as the patient care provider 10 may access the medication requisition database 90 to obtain information regarding the medication requisition during fulfillment by the remote fulfillment site. However, even in the case of an onsite fulfillment site (e.g., fulfillment site 55), medication requisition metadata may still be provided to the medication requisition database (e.g., to maintain records corresponding to the medication requisition).

The medication requisition metadata may include data corresponding to a plurality of different classes of data relating to the medication requisition including:
  medication source data;
  chain of custody data;
  fulfillment quality data; or
  environmental data.

The medication source data may include data indicative of, for example:
  a manufacturer of a component of the contained medication unit corresponding to the medication requisition,
  a lot number of a component of the contained medication unit corresponding to the medication requisition,
  an expiration date of a component of the contained medication unit corresponding to the medication requisition,
  a serial number of a component of the contained medication unit corresponding to the medication requisition, or
  a drug code indicative of the identity of a component of the contained medication unit corresponding to the medication requisition.

The chain of custody data may include data indicative of, for example:
  a listing of entities in possession of a component of the contained medication unit corresponding to the medication requisition or the contained medication unit corresponding to the medication requisition,
  a listing of users that have taken an action with respect to the contained medication unit corresponding to the medication requisition, wherein the listing of users is correlated to specific actions taken by each user, or
  tracking information corresponding to physical movement of a component of the contained medication unit corresponding to the medication requisition or the contained medication unit corresponding to the medication requisition.

The fulfillment quality data may include data indicative of, for example:
  image data corresponding with a component of the contained medication unit corresponding to the medication requisition or the contained medication unit corresponding to the medication requisition,
  scanned data obtained from a component of the contained medication unit corresponding to the medication requisition,
  analytic data regarding a component of the contained medication unit corresponding to the medication requisition or the contained medication unit corresponding to the medication requisition,
  pharmacist review data corresponding with at least one pharmacist review of a component of the contained medication unit corresponding to the medication requisition or the contained medication unit corresponding to the medication requisition,
  compliance data corresponding with best practices associated with a component of the contained medication unit corresponding to the medication requisition or the contained medication unit corresponding to the medication requisition;
  sterility assessment data corresponding to a component of the contained medication unit corresponding to the medication requisition or the contained medication unit corresponding to the medication requisition,
  a listing of actions corresponding to a component of the contained medication unit corresponding to the medication requisition or the contained medication unit corresponding to the medication requisition,
  time stamp data corresponding to actions corresponding to a component of the contained medication unit corresponding to the medication requisition or the contained medication unit corresponding to the medication requisition, or
  a listing of life cycle events taken with respect a component of the contained medication unit corresponding to the medication requisition or the contained medication unit corresponding to the medication requisition.

The environmental data may be indicative of, for example:
  a temperature to which a component of the contained medication unit corresponding to the medication requisition or the contained medication unit corresponding to the medication requisition has been exposed,
  a temperature to which and corresponding time period for which a component of the contained medication unit corresponding to the medication requisition or the contained medication unit corresponding to the medication requisition has been exposed,
  whether a component of the contained medication unit corresponding to the medication requisition or the contained medication unit corresponding to the medication requisition is refrigerated,
  whether a component of the contained medication unit corresponding to the medication requisition or the contained medication unit corresponding to the medication requisition is frozen,
  a temperature profile experienced by a component of the contained medication unit corresponding to the medication requisition or the contained medication unit corresponding to the medication requisition, or
  accelerometer data corresponding to forces experienced by a component of the contained medication unit corresponding to the medication requisition or the contained medication unit corresponding to the medication requisition.

Accordingly, the fulfillment site that fulfills the medication requisition, be it an onsite fulfillment site 55 or a remote fulfillment site 60*a* or 60*b*, may provide medication requisition metadata in connection with the medication requisition.

In addition, in the case of the remote fulfillment site 60*a* or 60*b*, the remote fulfillment site may dispatch the medication requisition for physical delivery to patient care provider 10 for administration to the patient 70. Accordingly, the remote fulfillment sites 60*a* and 60*b* may be able to ship or otherwise physically dispatch the medication requisition to patient care provider 10. As such, the remote fulfillment site may utilize dedicated delivery vehicles and/or third party delivery services. In either or any regard, the mode of physically dispatching the medication requisition may include tracking data associated with the transport of the medication requisition.

In an embodiment, a remote fulfillment site may collectively send more than one medication requisition to the patient care provider 10. In this regard, a kit may be sent from the remote fulfillment site to the patient care provider 10. The kit may include a plurality of medication requisitions destined to the same patient care provider 10. As such, the kit may include a kit identification. Each medication requisition disposed in the kit may be correlated to the kit identification. In this regard, once the kit is received at the patient care provider, the kit identification may be used to determine that each of the plurality of medication requisitions associated with the kit have likewise been received. Furthermore, any one of the medication requisitions identified that is associated with the kit may indicate that each of the other medication requisitions associated with the kit have been received.

Accordingly, the remote fulfillment site may also provide to the medication requisition management network 80 the kit identification and correlated medication requisitions associated with the kit. In turn, the kit identification and data regarding the correlated medication requisitions associated with the kit may be provided to the patient care provider 10 and/or the medication requisition database 90 for storage.

In an embodiment, each fulfillment site may include a medication requisition management client. The medication requisition management client may be in operable communication with the medication requisition management network 80, wherein the medication requisition management client is operable to receive/send data corresponding with a medication requisition to/from from the medication requisition management network 80. In this regard, the medication requisition management client may be employed by the fulfillment site to assist in the preparation of the medication unit associated with a medication requisition in a manner that also generates or documents medication requisition metadata as described above.

Figure 2:
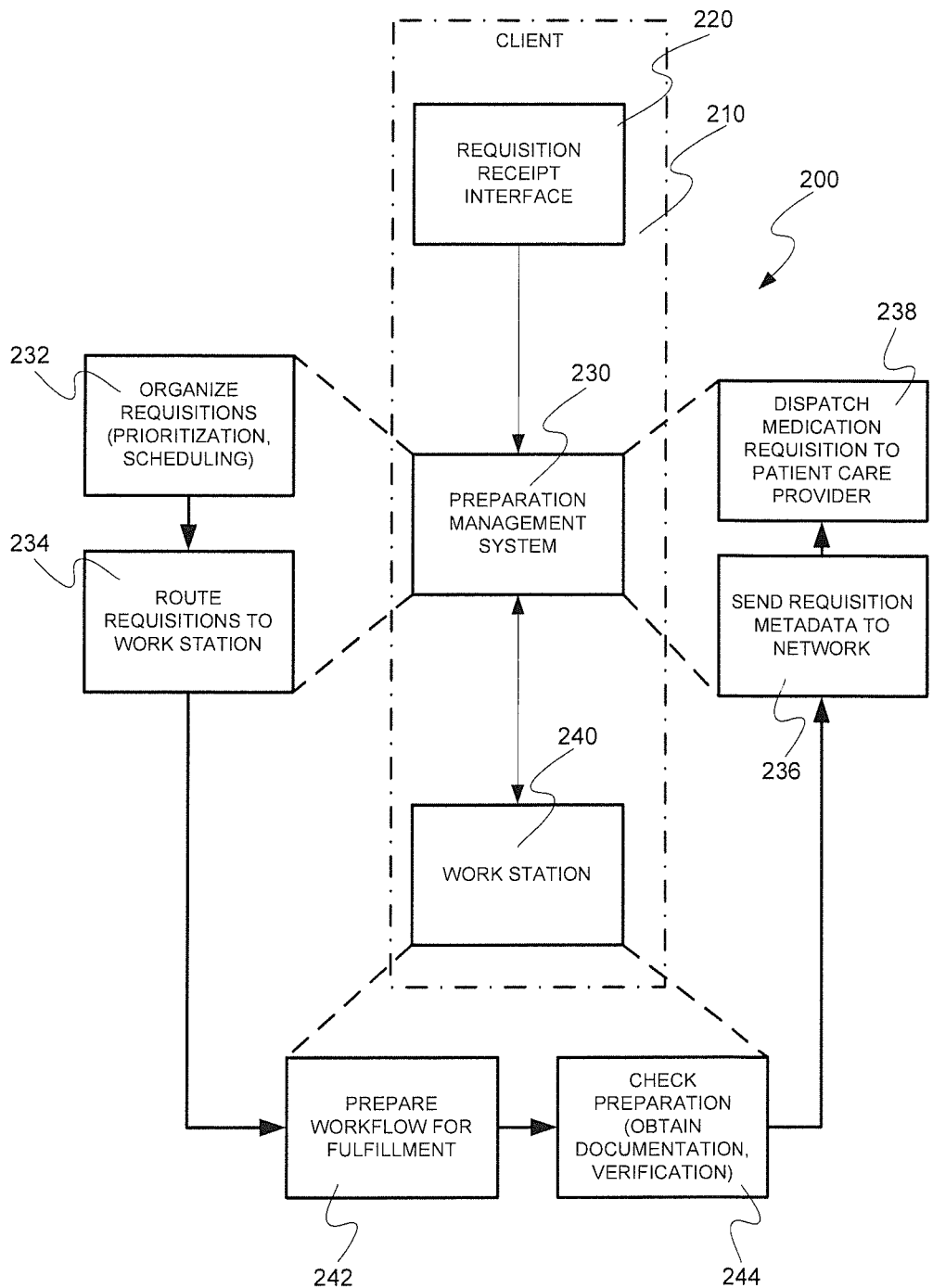
FIG. 2 illustrates an embodiment for use in the system embodiment of FIG. 1.

FIG. 2 illustrates an embodiment of a medication requisition management client 210 that may be used at a fulfillment site 200 to assist in the preparation and/or management of medication requisitions. The client 210 may be a thick or thin client resident at a fulfillment site. For example, the client to 10 may be a thin client such as a web browser executing on a device at the fulfillment site with access to a web-based service. In this regard, a requisition receipt interface 220 may be provided to receive medication requisitions. In furtherance to the above, the requisition receipt interface 220 may communicate directly with a requisition router 40 or may be in operative communication with the requisition router 40 by way of the medication requisition management network 80.

The medication requisitions may be passed on to a requisition preparation management system 230. The requisition preparation management system 230 may be operable to organize 232 medication requisitions received at the medication requisition preparation management client 210. The organization may include prioritization, scheduling, or other tasks associated with the organization or management of medication requisitions. The medication requisition preparation management client 230 may also be operative to route 234 medication requisitions to an appropriate work station 240. In this regard, a plurality of work stations 240 may be provided that may each be suited for different tasks or work flows. As such, depending on the nature of a medication requisition, a particular type of work station 240 may be used to prepare the requisition.

In this regard, the medication requisition preparation management system 230 may be in operative communication with one or more work stations 240. The routing 234 of medication requisitions may be at least partially based on the nature or type of the medication unit and the capabilities of the various work stations 240. In an embodiment, other parameters such as technician schedules, work station schedules, work station location, or other information may be used alone or in combination to route 234 medication requisitions to a particular work station 40.

At the work station 240, a work flow may be prepared 242 that may be used for the preparation of the medication requisition. In this regard, a work flow that is specific to the medication requisition currently being prepared at the work station 240 may be generated and presented to a user at the work station 240. Accordingly, the user may follow a sequence of steps to prepare the medication unit corresponding to the medication requisition based on the prepared work flow presented.

During and/or after the preparation of the medication requisition, the work station 240 may be used to assist in checking 244 the preparation of the medical order. For example, the work station 240 may allow for recording of documentation regarding the preparation of the medication unit such as, for example, barcode scans of products, images of apparatus during or after use in the preparation of the medication unit, or other information related to the preparation of the medication unit. This data may correspond to at least a portion of the medication requisition metadata described above.

Such information collected for the checking 244 may be stored for viewing by appropriate personnel (e.g., a pharmacist) so that the pharmacist may verify the prepared medication requisition prior to the medication requisition leaving the fulfillment site 200. In an embodiment, the information and/or data collected at the work station 240 may be made available to a pharmacist via a network (e.g., the medication requisition management network 80). In this regard, it may be also appreciated that alternate or additional pharmacists (e.g., a pharmacist at the patient care provider 10) may provide concurrent or additional reviews of the medication unit associated with a medication requisition being fulfilled. In any regard, the pharmacist tasked with verifying a medication requisition may access the information and/or data remotely (e.g., in a location in the fulfillment site but outside the room where the medication unit has been prepared or even entirely removed from the fulfillment site premises) via the network 80.

Once the medication requisition has been prepared in accordance with the prepared 242 work flow and checked 242 at workstation 240, the medication requisition preparation management system 230 may send medication requisition metadata to the medication requisition management network 80 for storage in the medication requisition database 90 and/or permission to patient care provider 10. In turn, the medication requisition preparation management system 230 may manage dispatching 238 the medication requisition to the patient care provider 10. In this regard, the medication requisition preparation management system 230 may oversee physical shipment of the medication requisition to the patient care provider 10 in addition to providing data regarding the dedication requisition to the medication requisition management network 80.

Patient care providers currently have limited access to sources of medication units needed for patient care. This limitation derives primarily from the current limitations of their systems and processes to enable only static choices for each specific type of medication unit. These static choices are often determined through completely manual procurement/evaluation processes, and are only revisited episodically. This often results in higher than optimal costs for meeting the provider's needs for medication units, and seriously limits the ability of the patient care provider to efficiently and rapidly respond to events—such as drug shortages or local events that generate significant supply/demand changes—that require a different sourcing approach.

Upon implementation of the present invention, patient care providers will be able to define a set of dynamically-applied rules for selecting sources of each specific type of medication units. This dynamic response capability will enable needs for medication units to be more reliably met on a timely basis, more efficient and effective response for local events and supply issues, and lower cost of medication units taking into consideration new sources of supply.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A system for fulfillment of a medication requisition to obtain a contained medication unit to be dispensed by a patient care provider for administration to a patient, comprising:
    a requisition generator for use by the patient care provider to generate a medication requisition, in an automated or partially automated manner, for the contained medication unit for administration to a patient, wherein the requisition generator is operable to derive data from a data stream to generate the medication requisition;
    requisition fulfillment logic comprising an algorithm for use by the patient care provider and executed by a computer-based tool to process the medication requisition to provide decision data for use in selecting one of a plurality of fulfillment sites to fulfill the medication requisition,
    wherein each of the plurality of fulfillment sites affirmatively sends both medication requisition fulfillment cost data and medication requisition fulfillment timing data to the requisition fulfillment logic, and
    wherein the decision data is based at least in part on one of medication requisition fulfillment cost data or medication requisition fulfillment timing data corresponding to and provided by each of the plurality of fulfillment sites;
    a medication requisition database, wherein each of said plurality of fulfillment sites is operable to provide medication requisition metadata for storage in the medication requisition database regarding medication requisition fulfillment at the fulfillment site; and
    a requisition router in communication with a medication requisition management network to route the medication requisition to a medication requisition preparation management system of a selected fulfillment site selected from the plurality of fulfillment sites by way of the medication requisition management network for fulfillment of the medication requisition, wherein the medication requisition preparation management system is in operative communication with a work station at the selected fulfillment site to prepare the contained medication unit based on the medication requisition routed to the selected fulfillment site, wherein the work station prepares and presents to a user of the work station a work flow specific to the medication requisition being prepared at the work station including a sequence of steps to prepare the contained medication unit corresponding to the medication requisition based on the work flow, wherein the work station records, utilizing data collection tools, medication requisition metadata comprising bar code scans of products and images of apparatus during or after use in the preparation of the contained medication unit documenting preparation of the contained medication unit in accordance with the work flow, wherein the contained medication unit is physically obtained by the patient care provider from the selected fulfillment site for dispensing and for administration to the patient, and wherein the selected fulfillment site provides the requisition router with medication requisition metadata via the medication requisition management network regarding the preparation of the contained medication unit for storage in the medication requisition database.

2. The system of claim 1, wherein at least one of the plurality of fulfillment sites is a remote fulfillment site that is remotely located relative to the patient care provider.

3. The system of claim 2, wherein the requisition generator, requisition fulfillment logic, and requisition router are located at the patient care provider.

4. The system of claim 3, wherein another one of the plurality of fulfillment sites is at a patient care provider site corresponding to the patient care provider.

5. The system of claim 4, wherein the patient care provider comprises an entity authorized by a governing regulatory body to prepare medication requisitions.

6. The system of claim 1, wherein the patient care provider comprises one or more of the following:
    an acute care site;
    a hospital;
    a home infusion pharmacy;
    a physician office; or
    a free standing infusion clinic.

7. The system of claim 1, wherein the patient care provider comprises a hospital having an affiliated pharmacy.

8. The system of claim 1, wherein the medication requisition database is operable to store the medication requisition metadata in corresponding relation to a medication requisition record.

9. The system of claim 8, wherein the contained medication unit comprises at least one of the following:
    a patient specific unit comprising a medication unit designated for administration to a specific patient;
    a non-patient specific unit comprising a medication unit to be subsequently designated for administration to a specific patient; or, a medication component source unit to be used in the preparation of a patient specific unit or a non-patient specific unit.

10. The system of claim 9, wherein the contained medication unit comprises a nutritional supplement or a component of a nutritional supplement that requires administration by the patient care provider.

11. The system of claim 8, wherein the contained medication unit is received by the patient care provider from the remote fulfillment site, wherein the contained medication unit is associated with a kit comprising a plurality of contained medication units, wherein the plurality of contained medication units have corresponding medication requisitions that are associable with a kit identifier corresponding with the kit, and wherein said kit identifier comprises a machine-readable marking on a container used for handling the plurality of contained medication units.

12. The system of claim 8, wherein the contained medication unit is to be administered to the patient at the patient care provider site.

13. The system of claim 8, wherein the medication requisition fulfillment cost data and the medication requisition fulfillment timing data are stored in the medication requisition database.

14. The system of claim 1, wherein the medication requisition fulfillment timing data comprises at least one of:
   medication requisition fulfillment lead time data;
   medication requisition availability data;
   medication requisition delivery schedule data;
   medication requisition efficacy timing data; or
   medication unit component efficacy timing data.

15. The system of claim 14, wherein each of the plurality of fulfillment sites provides a portion of the medication requisition fulfillment cost data and medication requisition fulfillment timing data corresponding to the respective fulfillment site to the medication requisition database.

16. The system of claim 1, wherein requisition fulfillment logic is at least in part customizable by the patient care provider.

17. The system of claim 1, wherein the algorithm is for use in processing the medication requisition in relation to both stored medication requisition fulfillment cost data and stored medication requisition timing data.

18. The system of claim 17, wherein the algorithm comprises selectable weighting parameters associated with each of the medication requisition fulfillment cost data and the medication requisition fulfillment timing data.

19. The system of claim 18, wherein the weighting parameters associated with the medication requisition fulfillment cost data and the medication requisition fulfillment timing data are customizable by the patient care provider.

20. The system of claim 19, wherein the patient care provider defines additional logic parameters for use by the requisition fulfillment logic.

21. The system of claim 1, wherein the requisition fulfillment logic is operable to automatically select the selected fulfillment site at least partially based on the decision data.

22. The system of claim 21, wherein the requisition router is operable to automatically route the medication requisition to the selected fulfillment site for fulfillment of the medication requisition.

23. The system of claim 1, wherein the selected fulfillment site is adapted to selectively, automatically, or semi-automatically communicate a requisition rejection to the requisition fulfillment logic and medication requisition database in relation to the medication requisition, wherein the requisition fulfillment logic is operable to reprocess the medication requisition to generate decision data for use in the selection of another one of the plurality of fulfillment sites for fulfillment of the medication requisition.

24. The system of claim 1, wherein the patient care provider is capable of accessing at least a portion of the medication requisition metadata from the medication requisition database.

25. The system of claim 24, wherein the medication requisition metadata comprises at least one of the following types of data:
   medication source data indicative of at least one of:
      a manufacturer of a component of the contained medication unit corresponding to the medication requisition,
      a lot number of a component of the contained medication unit corresponding to the medication requisition,
      an expiration date of a component of the contained medication unit corresponding to the medication requisition,
      a serial number of a component of the contained medication unit corresponding to the medication requisition, or
      a drug code indicative of an identity of a component of the contained medication unit corresponding to the medication requisition;
   chain of custody data indicative of at least one of:
      a listing of entities in possession of a component of the contained medication unit corresponding to the medication requisition or the contained medication unit corresponding to the medication requisition,
      a listing of users that have taken an action with respect to the contained medication unit corresponding to the medication requisition, wherein the listing of users is correlated to specific actions taken by each user, or
      tracking information corresponding to physical movement of a component of the contained medication unit corresponding to the medication requisition or
   the contained medication unit corresponding to the medication requisition; fulfillment data indicative of at least one of:
      image data corresponding with a component of the contained medication unit corresponding to the medication requisition or the contained medication unit corresponding to the medication requisition,
      scanned data obtained from a component of the contained medication unit corresponding to the medication requisition,
      analytic data regarding a component of the contained medication unit corresponding to the medication requisition or the contained medication unit corresponding to the medication requisition,
      pharmacist review data corresponding with at least one pharmacist review of a component of the contained medication unit corresponding to the medication requisition or the contained medication unit corresponding to the medication requisition,
      compliance data corresponding with best practices associated with a component of the contained medication unit corresponding to the medication requisition or the contained medication unit corresponding to the medication requisition,
      sterility assessment data corresponding to a component of the contained medication unit corresponding to the medication requisition or the contained medication unit corresponding to the medication requisition,
      a listing of actions corresponding to a component of the contained medication unit corresponding to the medication requisition or the contained medication unit corresponding to the medication requisition, time stamp data corresponding to actions corresponding to a component of the contained medication unit corresponding to the medication requisition or the contained medication unit corresponding to the medication requisition, or a listing of life cycle events taken with respect to a component of the contained medication unit corresponding to the medication requisition or the contained medication unit corresponding to the medication requisition; or environmental data indicative of at least one of:

a temperature to which a component of the contained medication unit corresponding to the medication requisition or the contained medication unit corresponding to the medication requisition has been exposed, a temperature to which and corresponding time period for which a component of the contained medication unit corresponding to the medication requisition or the contained medication unit corresponding to the medication requisition has been exposed, whether a component of the contained medication unit corresponding to the medication requisition or the contained medication unit corresponding to the medication requisition is refrigerated, whether a component of the contained medication unit corresponding to the medication requisition or the contained medication unit corresponding to the medication requisition is frozen, a temperature profile experienced by a component of the contained medication unit corresponding to the medication requisition or the contained medication unit corresponding to the medication requisition, or accelerometer data corresponding to forces experienced by a component of the contained medication unit corresponding to the medication requisition or the contained medication unit corresponding to the medication requisition.

26. The system of claim 1, further comprising:

a distributed medication requisition management system comprising a distributed medication requisition management client at each of the plurality of fulfillment sites in operative communication with the requisition router to receive the medication requisition from the requisition router.

27. The system of claim 26, further comprising:

the medication requisition management network at least comprising the distributed medication requisition management clients, the medication requisition database, and the requisition router.

28. The system of claim 27, wherein at least a portion of the medication requisition fulfillment cost data and the medication requisition fulfillment timing data is located at a separate physical location.

29. The system of claim 28, wherein the medication requisition database is operative to store the medication requisition in particular, wherein the medication requisition database is operative to store the medication requisition fulfillment cost data and/or wherein the medication requisition database is operative to store the medication requisition fulfillment timing data.

30. The system of claim 29, wherein the medication requisition database stores the medication requisition metadata in corresponding relation to the medication requisition.

31. The system of claim 1, wherein the selected fulfillment site provides medication requisition metadata to the medication requisition database.

32. A distributed medication requisition management system, comprising:

a requisition generator to generate a medication requisition for a contained medication unit for dispensing by a patient care provider;

a medication requisition database operable to store the medication requisition;

a plurality of medication requisition management clients resident at a plurality of fulfillment sites capable of fulfilling the medication requisition;

a medication requisition management network in operative communication with each of the plurality of medication requisition management clients, the medication requisition database, and the requisition generator, wherein the medication requisition management network is operable to provide the medication requisition to a medication requisition preparation management system of a selected fulfillment site of the plurality of fulfillment sites, wherein each of the plurality of fulfillment sites affirmatively sends both medication requisition fulfillment cost data and medication requisition fulfillment timing data to the medication requisition management network, and wherein the medication requisition preparation management system is in operative communication with a work station at the selected fulfillment site to prepare a contained medication unit based on the medication requisition routed to the selected fulfillment site;

wherein the work station prepares and presents to a user of the work station a work flow specific to the medication requisition being prepared at the work station including a sequence of steps to prepare the contained medication unit corresponding to the medication requisition based on the work flow, wherein the work station records, utilizing data collection tools, medication requisition metadata comprising bar code scans of products and images of apparatus during or after use in the preparation of the contained medication unit documenting preparation of the contained medication unit in accordance with the work flow; and wherein the patient care provider physically obtains the contained medication unit corresponding with the medication requisition from the selected fulfillment site for dispensing and administration to the patient, and wherein the selected fulfillment site provides medication requisition metadata regarding the preparation of the contained medication unit to the medication requisition management network for storage in the medication requisition database in corresponding relation to the medication requisition.

33. A method for fulfillment of a medication requisition to be dispensed by a patient care provider for administration to a patient, comprising:

generating a medication requisition by use of a requisition generator coupled with a patient care provider, said medication requisition being for a contained medication unit for administration to a patient;

processing the medication requisition by use of requisition fulfillment logic by the patient care provider and executed by a computer-based tool, said processing providing decision data for use in selecting one of a plurality of fulfillment sites to fulfill the medication requisition, wherein each of the plurality of fulfillment sites affirmatively sends both medication requisition fulfillment cost data and medication requisition fulfillment timing data to the requisition fulfillment logic, and wherein the decision data is based at least in part on one of medication requisition fulfillment cost data or medication requisition fulfillment timing data received from and corresponding to each of the plurality of fulfillment sites;

routing the medication requisition by a requisition router, in communication with a medication requisition management network, to a medication requisition preparation management system of a selected fulfillment site selected from the plurality of fulfillment sites by way of the medication requisition management network for preparation of the contained medication unit according to the medication requisition, wherein the medication requisition preparation management system is in operative communication with a work station at the selected fulfillment site to prepare the contained medication unit based on the medication requisition, wherein the work station prepares and presents to a user of the work station a work flow specific to the medication requisition being prepared at the work station including a sequence of steps to prepare the contained medication unit corresponding to the medication requisition based on the work flow, wherein the work station records, utilizing data collection tools, medication requisition metadata comprising bar code scans of products and images of apparatus during or after use in the preparation of the contained medication unit documenting preparation of the contained medication unit in accordance with the work flow;

physically receiving at the patient care provider from the selected fulfillment site the contained medication unit along with medication requisition metadata via the medication requisition management network regarding the preparation of the contained medication unit; and storing the medication requisition metadata regarding the preparation of the contained medication unit in a medication requisition database.

34. The method of claim 33, further comprising:

selecting automatically, by operation of said requisition fulfillment logic, the selected fulfillment site at least partially based on the decision data.

35. The method of claim 34, further comprising:

routing automatically, by operation of said router, the medication requisition to the selected fulfillment site for fulfillment of the medication requisition.

* * * * *